(12) United States Patent
Fang-Yen et al.

(10) Patent No.: US 12,089,566 B2
(45) Date of Patent: Sep. 17, 2024

(54) SYSTEMS AND METHODS FOR AUTOMATED IMAGING AND MANIPULATION OF SMALL ANIMALS

(71) Applicant: THE TRUSTEES OF THE UNIVERSITY OF PENNSYLVANIA, Philadelphia, PA (US)

(72) Inventors: Christopher Fang-Yen, Philadelphia, PA (US); Anthony Fouad, Philadelphia, PA (US)

(73) Assignee: The Trustees of the University of Pennsylvania, Philaelphia, PA (US)

( * ) Notice: Subject to any disclaimer, the term of this patent is extended or adjusted under 35 U.S.C. 154(b) by 976 days.

(21) Appl. No.: 17/099,285

(22) Filed: Nov. 16, 2020

(65) Prior Publication Data
US 2021/0084867 A1    Mar. 25, 2021

Related U.S. Application Data

(63) Continuation-in-part of application No. PCT/US2020/038610, filed on Jun. 19, 2020.
(Continued)

(51) Int. Cl.
*A01K 29/00* (2006.01)
*A01K 67/033* (2006.01)
(Continued)

(52) U.S. Cl.
CPC ........ *A01K 29/005* (2013.01); *A01K 67/0336* (2013.01); *G01N 21/6458* (2013.01);
(Continued)

(58) Field of Classification Search
CPC ............ A01K 29/005; A01K 67/0336; G01N 21/6458; G01N 21/6486; G02B 21/16;
(Continued)

(56) References Cited

U.S. PATENT DOCUMENTS 3,775,256 A * 11/1973 Risinger ................ C12M 37/00
435/801
4,242,462 A * 12/1980 Thomas ................. C12M 33/02
435/309.3

(Continued)

FOREIGN PATENT DOCUMENTS

EP       1 502 649 A1     2/2005
JP       2004229634 A *  8/2004
(Continued)

OTHER PUBLICATIONS

Espacenet English Machine Translation of JP2004229634. (Year: 2004).*

(Continued)

*Primary Examiner* — Christine T Mui
*Assistant Examiner* — Kathryn Elizabeth Limbaugh
(74) *Attorney, Agent, or Firm* — Baker Botts, LLP

(57) ABSTRACT

The disclosed subject matter provides a system and methods for automated imaging and manipulation of small animals. In exemplary embodiments, the disclosed subject matter provides a motorized picking assembly, that is coupled to a processor and adapted to remove selected small animals from a source plate and transfer them to a destination plate. The disclosed subject matter provides methods, which include identifying at least one parameter for the small organisms, selecting organisms based on the parameter and transferring selected organisms from the source plate to the destination plate. In certain embodiments, the disclosed subject matter provides a handheld self-sterilizing loop tool for the manual manipulation of small organisms.

12 Claims, 21 Drawing Sheets

Related U.S. Application Data

(60) Provisional application No. 62/864,345, filed on Jun. 20, 2019.

(51) Int. Cl.
| | |
|---|---|
| *B25J 11/00* | (2006.01) |
| *C12M 1/34* | (2006.01) |
| *G01N 21/64* | (2006.01) |
| *G02B 21/16* | (2006.01) |
| *G02B 21/32* | (2006.01) |
| *G02B 21/36* | (2006.01) |

(52) U.S. Cl.
CPC ......... *G01N 21/6486* (2013.01); *G02B 21/16* (2013.01); *G02B 21/32* (2013.01); *G02B 21/365* (2013.01); *A61B 2503/40* (2013.01); *B25J 11/00* (2013.01); *C12M 41/00* (2013.01)

(58) Field of Classification Search
CPC .. G02B 21/32; G02B 21/365; A61B 2503/40; B25J 11/00; C12M 41/00
See application file for complete search history.

(56) References Cited

U.S. PATENT DOCUMENTS

| | | | |
|---|---|---|---|
| 2005/0026221 A1* | 2/2005 | Richmond | C12M 33/04 435/287.1 |
| 2008/0006653 A1* | 1/2008 | Dai | B01L 3/0268 222/75 |
| 2009/0000567 A1 | 1/2009 | Hadjioannou et al. | |
| 2010/0294947 A1* | 11/2010 | Oda | G01N 21/6456 250/200 |
| 2012/0189549 A1* | 7/2012 | Claridge-Chang | A01K 29/005 600/300 |
| 2014/0242570 A1* | 8/2014 | Botma | C12M 47/02 435/286.2 |
| 2015/0023566 A1 | 1/2015 | Fryshman | |
| 2016/0001039 A1 | 1/2016 | Armour et al. | |
| 2018/0221593 A1* | 8/2018 | Peh | A61M 1/3653 |
| 2020/0260685 A1* | 8/2020 | Slade | B25J 11/00 |
| 2021/0153507 A1* | 5/2021 | Zhang | C12N 1/205 |

FOREIGN PATENT DOCUMENTS

| | | |
|---|---|---|
| WO | WO 2018/134829 A1 | 7/2018 |
| WO | WO 2019/092417 A1 | 5/2019 |

OTHER PUBLICATIONS

Supplemental European Search Report dated Jun. 5, 2023 in Application No. EP 20826501.

International Search Report mailed Sep. 24, 2020 for International Application No. PCT/US2020/038610.

* cited by examiner

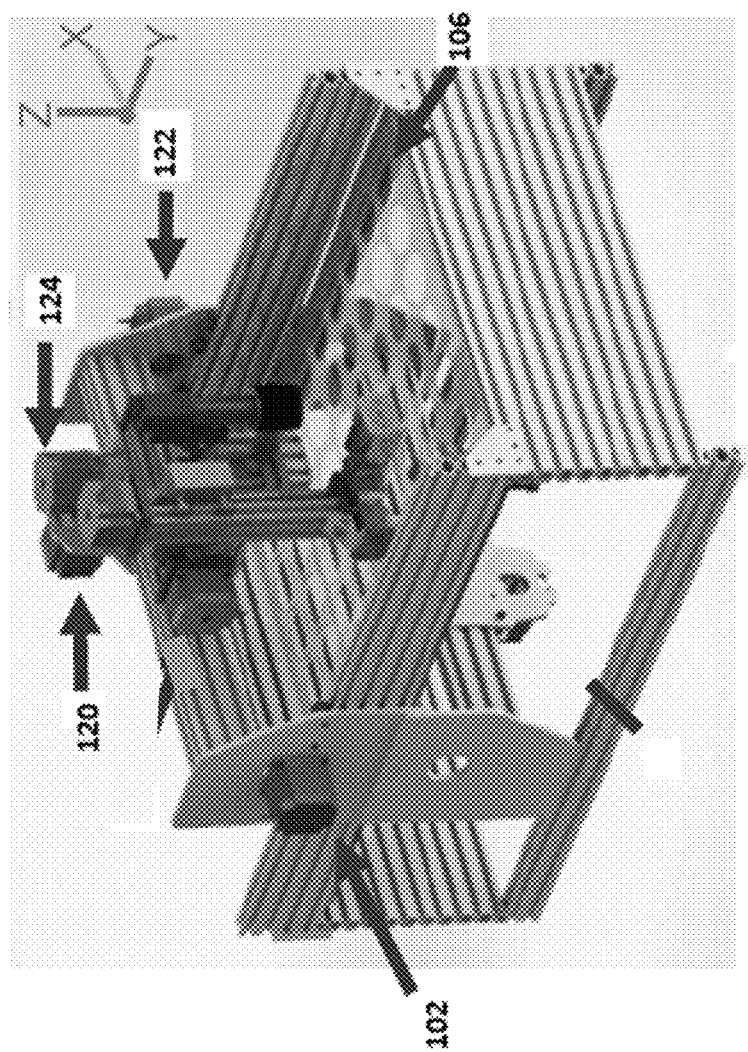

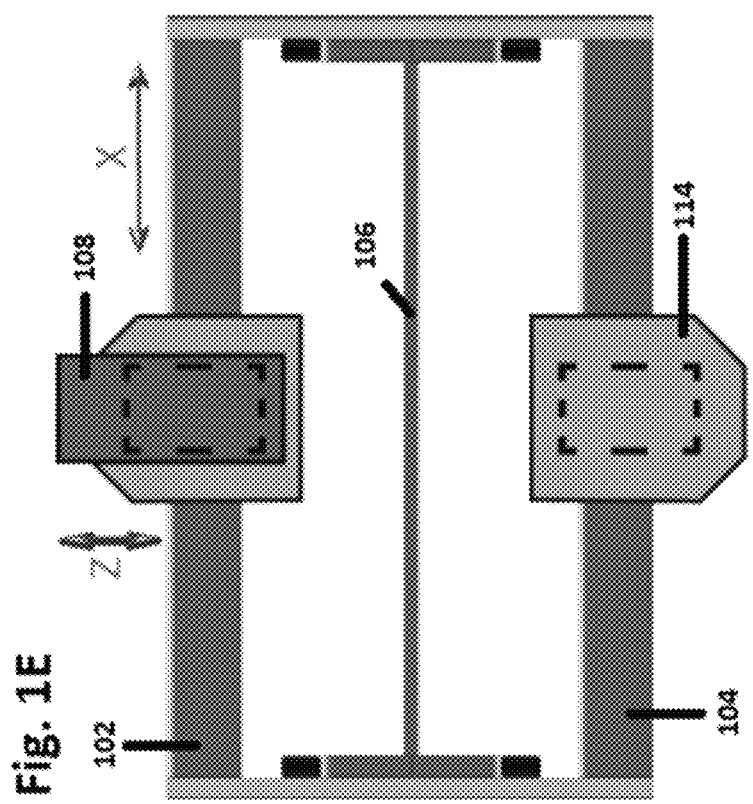

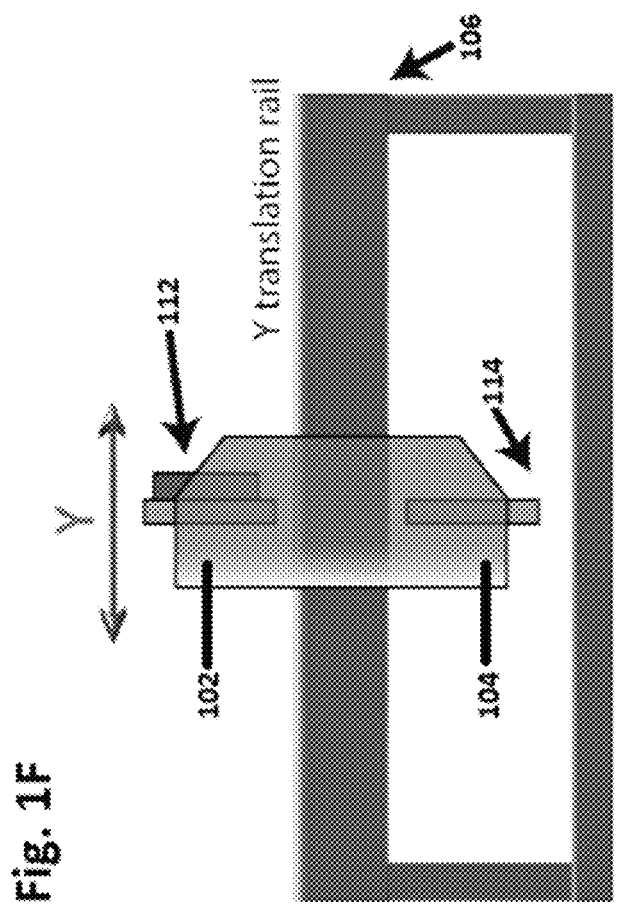

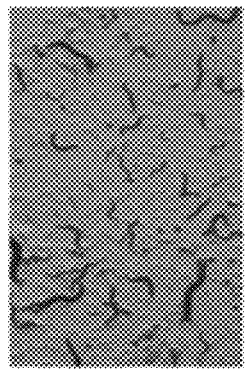
Fig. 2A Original image
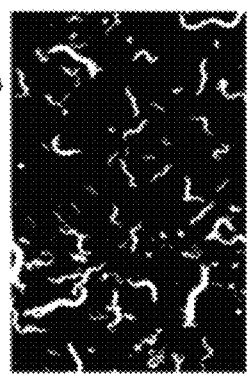
Fig. 2B Binarized image
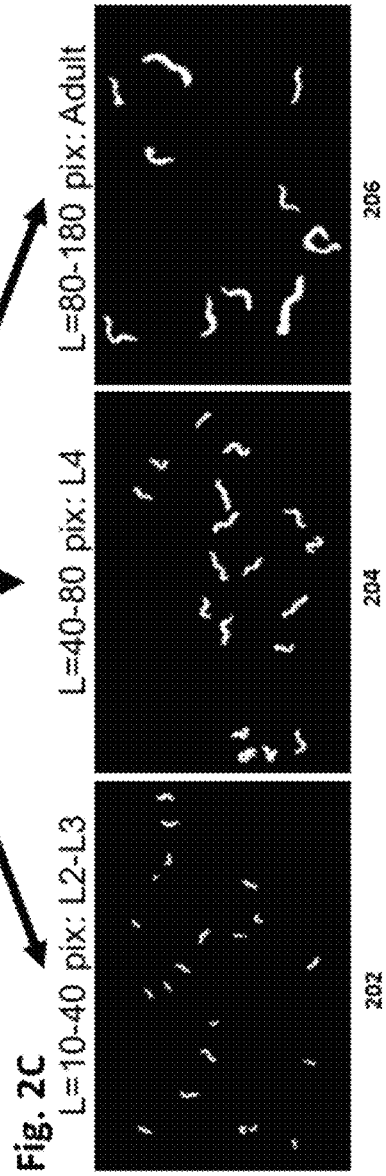
Fig. 2C
L=10-40 pix: L2-L3
L=40-80 pix: L4
L=80-180 pix: Adult

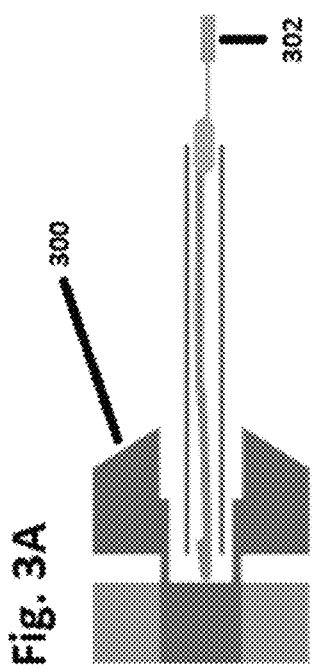

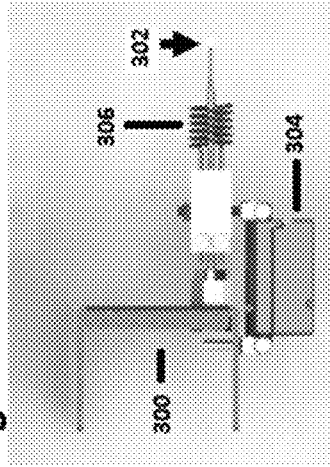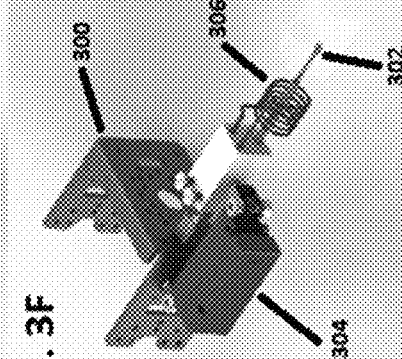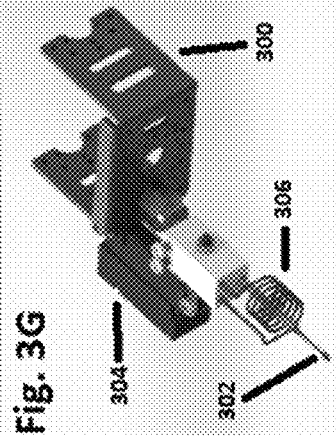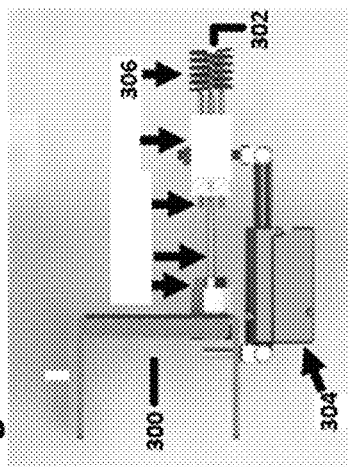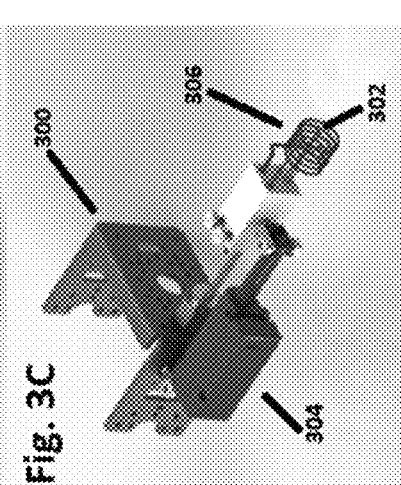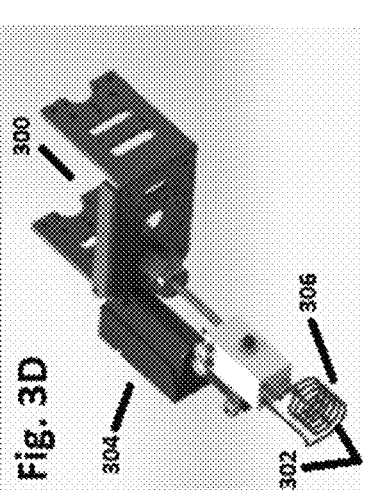

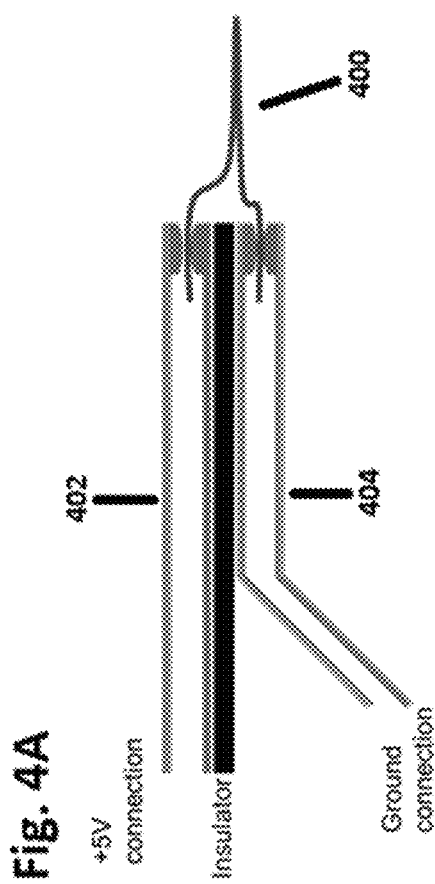

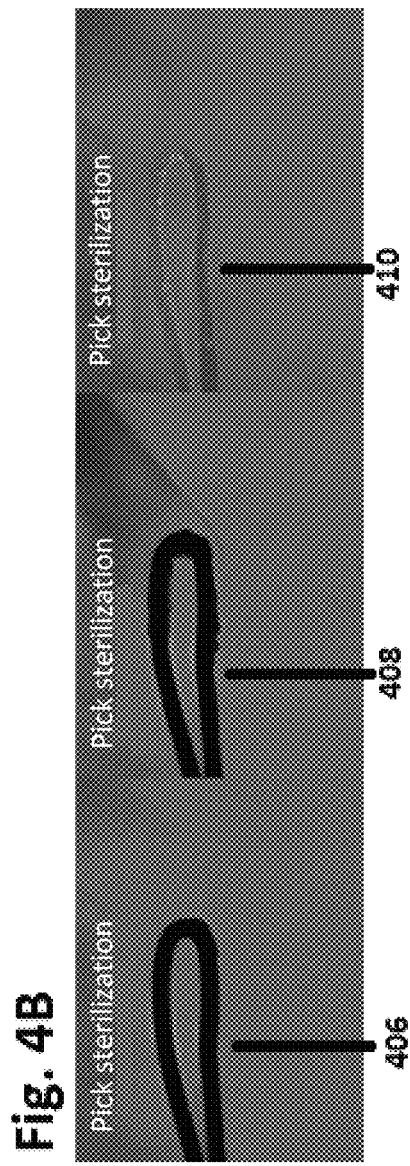

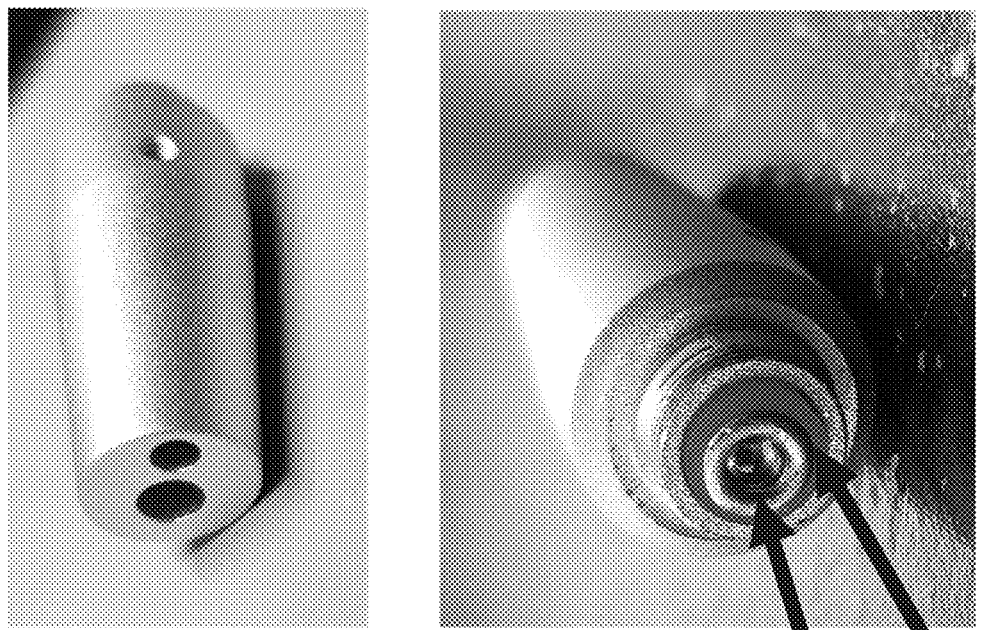
Fig. 10

SYSTEMS AND METHODS FOR AUTOMATED IMAGING AND MANIPULATION OF SMALL ANIMALS

CROSS-REFERENCE TO RELATED APPLICATION

This application is a continuation-in-part application of International Application No. PCT/US2020/038610 filed Jun. 19, 2020, which claims priority to U.S. Provisional Application Ser. No. 62/864,345 filed Jun. 20, 2019, the contents of which are hereby incorporated by reference in its entirety and from which priority is claimed.

GRANT INFORMATION

This invention was made with government support under NS115995 and NS109435 awarded by the National Institute of Health. The government has certain rights in the invention.

BACKGROUND

Certain techniques for imaging and manipulation of small organisms largely rely on manual procedures. Such manual procedures can require visual observation of small organisms, which confound large-scale imaging and manipulation of small organisms. Furthermore, manual procedures can depend on a researcher's ability to manually manipulate organisms and to identify phenotypes of interest. These techniques, therefore, can be prone to errors and require significant training, which imposes a high barrier to entry for researchers without the requisite experience. Even with highly experienced researchers, manual manipulation of small organisms requires significant labor.

Certain techniques rely on microfluidic methods, which can lead to difficulty accessing the small organisms within the microfluidic device and a limited degree of scalability. For example, while a microfluidic device can hold dozens of small organisms, scaling can require a large number of microfluidic devices.

Accordingly, there exists a need for an automated technique for imaging and manipulation of small organisms that is cost-effective and scalable. Such a technique would enable large-scale imaging and manipulation of small organisms and increase the productivity of researchers in performing these tasks. An automated technique would also allow for a larger number of conditions, larger sample sizes for each condition, and improved repeatability of results.

SUMMARY

Systems and methods for automated imaging and manipulation of a plurality of small animals are disclosed herein.

In exemplary embodiments, the disclosed subject matter provides a housing, comprising an upper gantry, a lower gantry, and a tray with an array of plates, wherein the tray includes at least one source plate and at least one destination plate. The tray is adapted to hold the plurality of small animals. A carriage, disposed within the upper gantry, is adapted to move relative to the tray. A camera, also disposed within the carriage, is adapted to acquire images of at least a portion of the small animals. A computational processor, coupled to the camera, is adapted to identify an approximate size and shape for at least a portion of the small animals from the images, and to select one or more small animals based therefrom on its size and shape. A motorized picking assembly, also disposed within the carriage, is coupled to the processor and adapted to remove the one or more selected small animals from the at least one source plate and effect transfer thereof to the at least one destination plate.

In some embodiments, the disclosed subject matter can include a capacitive touch sensor, disposed within the motorized picking assembly, adapted to detect contact between the motorized picking tool and a substrate on the at least one source plate, and/or detect proximity between the motorized picking tool and the substrate on the at least one source plate.

In some embodiments, the disclosed subject matter can include a lid manipulator, disposed within the carriage, adapted to take a lid off the at least one source plate before the motorized picking tool removes the one or more selected small animals and to replace the lid on the at least one source plate after the motorized picking tool removes the one or more selected small animals.

In some embodiments, a retractable heating coil, disposed within the motorized picking assembly, can be adapted to sterilize and clean the motorized picking tool through resistive heating and subsequent radiative and convective transfer of heat. The motorized picking tool can be loop-shaped such that a current is adapted to run through the motorized picking tool, wherein the current sterilizes and cleans the motorized picking tool through resistive heating. A heating coil, disposed within the tray, can be adapted to sterilize the motorized picking tool through resistive heating and subsequent radiative and convective transfer of heat.

In some embodiments, the disclosed subject matter can include an illuminator, disposed within the lower gantry, adapted to align with a position of the camera such that the illuminator illuminates upwards through the tray into the camera. At least one motor, disposed within the lower gantry, can be adapted to align the illuminator with the position of the camera. The motor can be adapted to move the carriage relative to the tray.

In some embodiments, the disclosed subject matter can include a fluorescence microscope with at least one channel, disposed within the carriage, adapted to measure fluorescence of at least a portion of the plurality of small animals. The processor can be coupled to the fluorescence microscope and further adapted to select the one or more small animals based on its fluorescence.

In certain embodiments, the disclosed subject can include a self-sterilizing and self-cleaning wire loop that can be a handheld tool for manual manipulation of small organisms. The self-sterilizing and self-cleaning loop can include a tip assembly and a handle. In non-limiting embodiments, the tip assembly can include a wire loop and contact pins, and the handle can include a battery. In some embodiments, the wire loop can be connected to the battery through the contact pins. When the user actuates a switch located on the device, the battery can generate a current that passes through the wire loop and the contact pins, heating the wire loop in excess of 1000 degrees F. or as needed for sterilization and cleaning.

In certain embodiments, the motorized picking assembly can include a tip assembly that includes a wire loop and contact pins. Contact pins allow the wire to be replaced by the user if the wire becomes damaged or fouled. A current can be generated to pass through the wire loop and contact pins hearing the wire loop for sterilization and cleaning.

In some embodiments, the disclosed subject matter provides methods, which include identifying at least one parameter for the small animals, selecting one or more small animals based the at least one parameter, removing the one or more selected small animals from at least one source plate, and effecting transfer thereof to at least one destination plate.

In some embodiments, the at least one parameter can be an approximate size and shape for at least a portion of the plurality of small animals. The at least one parameter can be a fluorescence signal for at least a portion of the plurality of small animals.

In some embodiments, the removing can also include lowering a motorized picking tool, removing the one or more selected small animals with the motorized picking tool, and raising the motorized picking tool. The disclosed subject matter can include heat sterilizing and cleaning the motorized picking tool. The disclosed subject matter can include detecting contact between the motorized picking tool and a substrate on the at least one source plate.

In some embodiments, the disclosed subject matter can include taking a lid off the tray before removing the one or more selected small animals from the at least one source plate. The disclosed subject matter can include replacing the lid on the tray after removing the one or more selected small animals from the at least one source plate.

In some embodiments, the approximate size and shape for the at least a portion of the plurality of small animals can be identified with a camera. The disclosed subject matter can include aligning an illuminator with a position of the camera such that the illuminator illuminates upwards into the camera. In certain embodiments, the disclosed method can further include manually manipulating the small organisms using a self-sterilizing and self-cleaning wire loop that can include a handheld tool. The self-sterilizing loop can include a tip assembly and a handle. In non-limiting embodiments, sterilizing the self-sterilizing loop can be performed by generating a current that passes through the wire loop and contact pins of the self-sterilizing loop. In some embodiments, a battery in the handle can generate the current for heating and sterilizing the wire loop.

In certain embodiments, the motorized picking assembly can include a tip assembly that includes a wire loop and contact pins. In non-limiting embodiments, the disclosed method can further include sterilizing and cleaning the tip assembly by generating a current that passes through a wire loop and contact pins heating the wire loop for sterilization.

The accompanying drawings, which are incorporated and constitute part of this disclosure, illustrate preferred embodiments of the invention and serve to explain the principles of the invention.

BRIEF DESCRIPTION OF THE DRAWINGS

FIGS. 1A-1F are schematic diagrams illustrating a system for automated imaging and manipulation of a plurality of small organisms in accordance with some embodiments of the disclosed subject matter.

FIGS. 2A-2C are diagrams depicting identification of an approximate size and shape for at least a portion of the plurality of small organisms and selection of one or more small organisms in accordance with some embodiments of the disclosed subject matter.

FIGS. 3A-3G are schematic diagrams illustrating an exemplary motorized picking assembly in accordance with some embodiments of the disclosed subject matter.

FIGS. 4A-4B are schematic diagrams illustrating an exemplary motorized picking tool in accordance with some embodiments of the disclosed subject matter.

FIG. 10 is an image depicting an exemplary exterior design of the handheld self-sterilizing loop device nose cone in accordance with some embodiments of the disclosed subject matter.

Figure 1A:
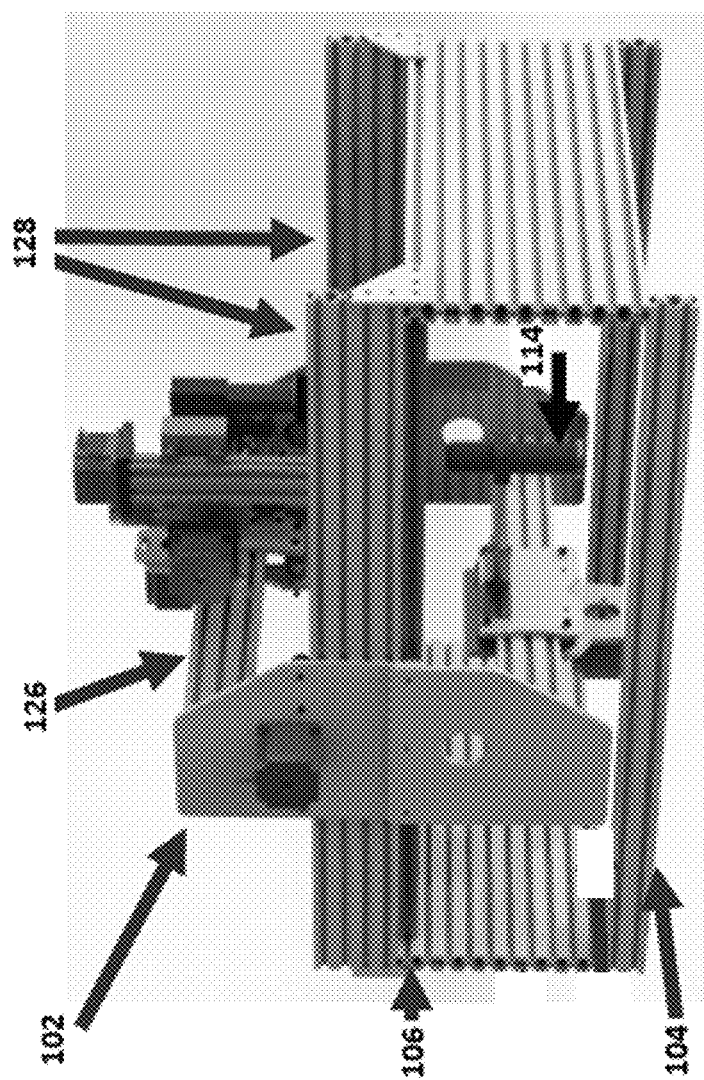
Figure 1C:
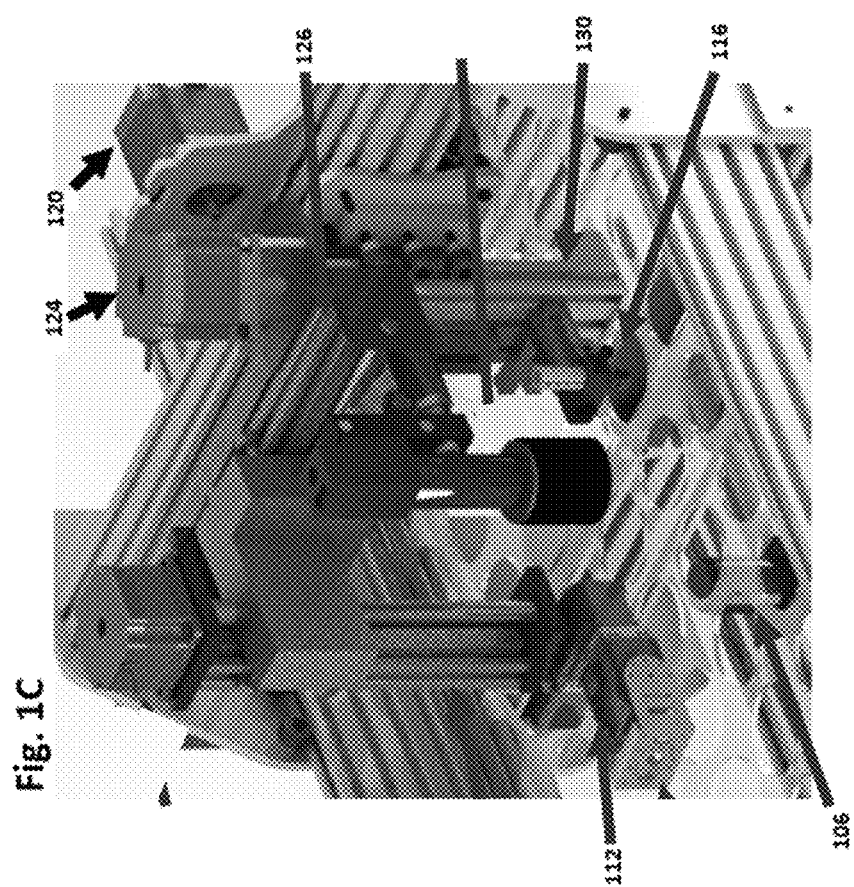

Throughout the drawings, the same reference numerals and characters, unless otherwise stated, are used to denote like features, elements, components or portions of the illustrated embodiments. Moreover, while the present invention will now be described in detail with reference to the Figs., it is done so in connection with the illustrative embodiments.

DETAILED DESCRIPTION

Techniques for automated imaging and manipulation of a plurality of small organisms are presented. The housing includes an upper gantry, a lower gantry, and a tray. The tray holds the plurality of small organisms. A carriage is disposed within the upper gantry and includes a camera and a motorized picking assembly. The carriage moves relative to the tray. The camera acquires images of at least a portion of the plurality of small organisms, e.g., one animal. A processor receives the images from the camera, identifies an approximate size and shape for at least a portion of the plurality of small organisms, and selects one or more small animals based therefrom based on its size, shape, or similarity to predetermined images as assessed by machine vision techniques including machine learning algorithms. The motorized picking assembly removes the one or more selected small animals from a source plate on the tray and effects transfer thereof to a destination plate on the tray.

FIGS. 1A-1F are schematic diagrams illustrating a system for automated imaging and manipulation of a plurality of small organisms in accordance with some embodiments of the disclosed subject matter. Small organisms can refer to animals such as nematodes and *Drosophila* larvae, or microbiological organisms including bacteria and fungi. A housing can include an upper gantry 102, a lower gantry 104, and a tray 106. The tray 106 can have an array of plates that can hold the plurality of small animals. For example, the tray can include plates in which the plurality of small animals lay on substrates. Small organisms can include model animals such as the roundworm *C. elegans* and the fruit fly *Drosophila melanogaster*. The tray 106 can include at least one source plate from which small animals are removed and at least one destination plate to which small animals are transferred.

The upper gantry 102 can have a carriage 108, in which a camera 110 and a motorized picking assembly 112 can reside. The carriage 108 can move relative to the tray 106. For example, at least one motor can move the carriage 108 relative to the tray 106. In some embodiments, an X-axis motor 120, a Y-axis motor 122, and a Z-axis motor 124 can move the carriage in three dimensions along an X-axis travel rail 126, a Y-axis travel rail 128, and a Z-axis travel rail 130, respectively.

The camera 110 can acquire images of the small animals. For example, the camera can be a 2592×1944 pixel GigE CMOS camera with a field of view of approximately 10 mm×8 mm. In some embodiments, the lower gantry 104 can have an illuminator 114. The illuminator 114 can align with a position of the camera such that the illuminator illuminates upwards through the tray into the camera. For example, the illuminator can be a 1 W LED.

FIGS. 2A-2C are diagrams depicting identification of approximate size and shape for at least a portion of the plurality of small animals and selection of one or more small animals based therefrom on its size and shape in accordance with some embodiments of the disclosed subject matter. The camera 110 can be coupled to a processor such that the camera 110 can send the images to the processor. FIG. 2A depicts an image of small animals. The processor can identify an approximate size and shape for at least a portion of the plurality of small animals from the images.

For example, the processor can use a machine vision algorithm that relies on simple shape analysis to identify the approximate size and shape for the small organisms. The processor can preprocess and smooth the images to correct for light intensity variations and noise across the image. A binary threshold can be applied to identify regions of dark pixels as depicted in FIG. 2B.

The geometry of each small animal can then be evaluated. First, the length of each small animal can be approximately half of the perimeter of the small organisms. Second, the width of the small animal can be approximated as the length of the small organisms divided by the area of the small animal. Third, the aspect ratio of the small animal can be the length of the small animal divided by the width of the small organisms. If small organisms are not identified, the binary threshold can be automatically adjusted until small organisms are found.

As shown in FIG. 2C, the small organisms can then be categorized and filtered based on their approximate size and shape. For example, *C. elegans* worms with a length of 10-40 pixels 202 can be identified as in the L2 or L3 stage, small animals with a length of 40-80 pixels 204 can be identified as in the L4 stage, and small animals with a length of 80-180 pixels 206 can be identified as in the Adult stage. The processor can then select one or more small animals based on its size and shape. For example, the processor can randomly select the one or more small animals based all of the small animals that comply with user requirements. A user can select a small animal via a user input. If none of the identified small animals comply with user requirements, the carriage 108 can move relative to the tray 106 until a suitable small animal is found or the entire tray has been identified.

In some embodiments, a fluorescence microscope with at least one channel can be disposed within the carriage and measure fluorescence of the small animals. For example, the fluorescence channel can have a single channel or multiple channels. The fluorescence microscope can then send the fluorescence measurements to the processor such that the processor can select the one or more small animals based on its fluorescence.

In some embodiments, a lid manipulator 116 can be disposed within the carriage 108. The lid manipulator 116 can take a lid off the at least one source plate before the motorized picking tool 118 removes the one or more selected small animals and replace the lid on the at least one source plate after the motorized picking tool 118 removes the one or more selected small animals. For example, the lid manipulator 116 can be a vacuum pump. To take a lid off the at least one source plate, the vacuum pump can be activated. The vacuum pump can engage and lift the lid. To replace the lid on the at least one source plate, the vacuum pump can be deactivated. Once the vacuum pump is deactivated, the lid can be released and returned to its original position.

Figure 1D:
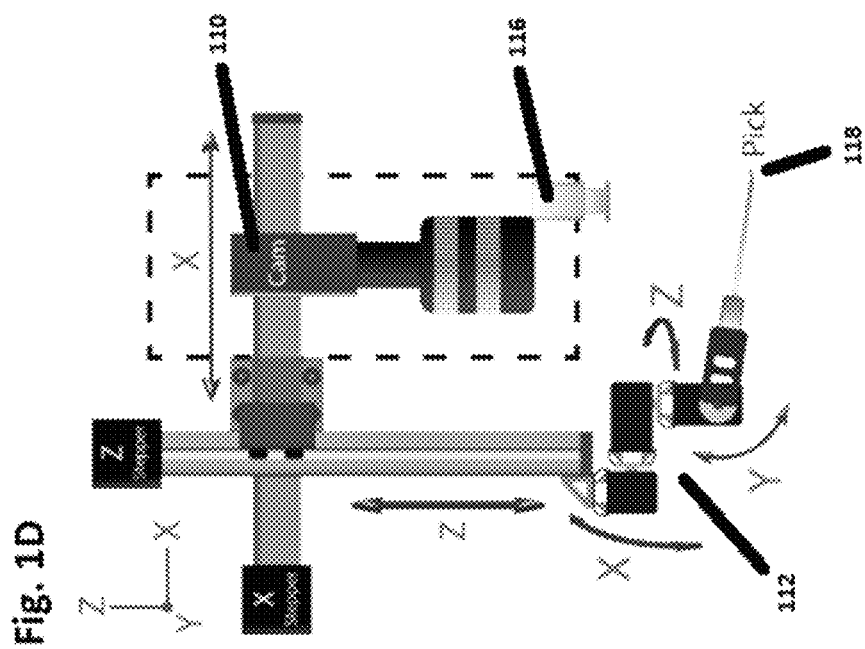

FIGS. 3A-3G are schematic diagrams illustrating an exemplary motorized picking assembly in accordance with some embodiments of the disclosed subject matter. The motorized picking assembly 112, 300 can be coupled to the processor. The motorized picking tool 118, 302 can be adapted to remove the one or more selected small animals from the at least one source plate and effect transfer thereof to the at least on destination plate. As shown in FIG. 3A, the motorized picking assembly 300 can include a motorized picking tool 302 and a linear actuator 304. For example, the motorized picking tool 302 can be a platinum-iridium wire of approximately 3 cm in length. For example, the tip of the motorized picking tool 302 can be flattened in to a standard worm picking shape. The motorized picking tool 302 can be actuated by the linear actuator 304. In some embodiments, the linear actuator 304 can be powered by at least one stepper motor and/or servo motor such that the motorized picking tool 302 can be moved along the X-axis and the Z-axis relative to the camera and rotated about any axis as shown in FIG. 1D. This movement can allow the motorized picking tool 302 to be positioned such that its tip is within the field of view of the camera 110, thereby allowing precise movements of the motorized picking tool 302 relative to the tray.

The motorized picking tool 302 can be sterilized prior to and between removing and transferring each small animal to prevent unintentional transfer of contaminants or worm larvae during subsequent removals and transfers. In some embodiments, as depicted in FIGS. 3B-3G, a retractable heating coil 306 can sterilize the motorized picking tool 302. For example, a current can be passed through the retractable heating coil 306 such that the retractable heating coil 306 can heat to a temperature in excess of 600° C. As shown in FIGS. 313-3D, the retractable heating coil 306 can be extended over the motorized picking tool 302. The retractable heating coil 306 can then be heated such that the motorized picking tool 302 is sterilized. Once the motorized picking tool 302 is sterilized, the retractable heating coil 306 can be retracted as shown in FIGS. 3E-3G. In some embodiments, a heating coil to sterilize the motorized picking tool 302 can be disposed in the tray such that the motorized picking tool 302 orients itself inside the coil, which is then heated.

FIGS. 4A-4B are schematic diagrams illustrating an exemplary motorized picking tool in accordance with some embodiments of the disclosed subject matter. In some embodiments, as depicted in FIGS. 4A-4B, the motorized picking tool 400 can be loop-shaped such that a current is adapted to run through the motorized picking tool 400, wherein the current sterilizes the motorized picking tool 400. As shown in FIG. 4A, a current can run from a first tube 402 through the motorized picking tool 400 to a second tube 404. For example, the first tube 402 can be wired to a 5V source and the second tube 404 can be connected to an electrical ground. When 5V is applied, the motorized picking tool 400 can be heated in excess of 1000° C. As shown in FIG. 4B, the motorized picking tool 400 can be coated with bacteria 406 before heating. While the motorized picking tool 400 is heated, the bacteria can begin to disintegrate 408. At the peak of heating, the motorized picking tool 400 can turn red hot 410 and be sterilized.

Figure 4D:
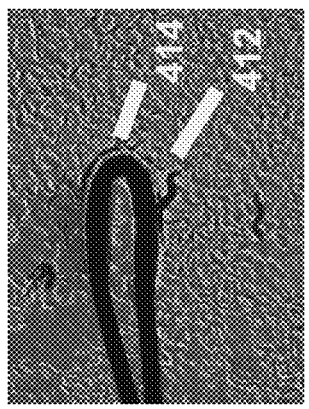
FIGS. 4C-4H are images showing an exemplary procedure to pick a small animal using a wire loop in accordance with some embodiments of the disclosed subject matter.
Figure 4F:
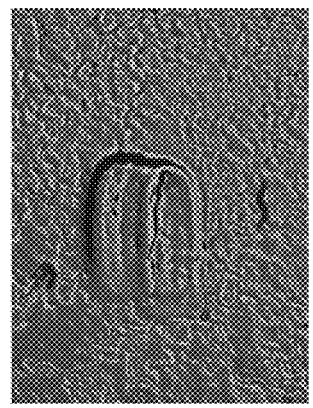
Figure 4H:
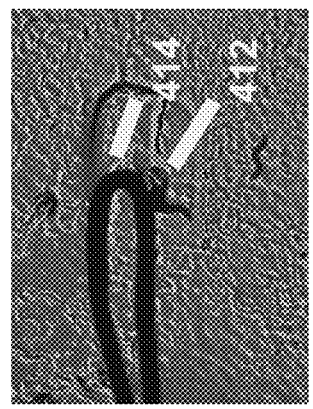
Figure 4C:
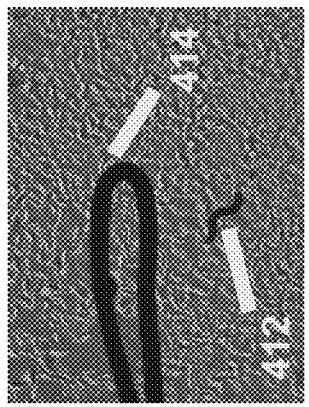
Figure 4E:

In certain embodiments, the disclosed loop-shaped picking to can be a wire loop. The wire loop can be used for removal and/or transfer of one or more selected small animals from a plate. For example, the wire loop can be used to remove and transfer *C. elegans*. As shown in FIG. 4C, at least one *C. elegans* 412 can be selected. The wire loop 414 can be lowered on to the surface of the plate containing *C. elegans*. For example, the wire loop 414 can be lowered until surface contact is detected by a capacitive touch sensor (FIG. 4D). The wire loop 414 can then be swept to remove the selected *C. elegans* 412 (FIG. 4E). The wire loop 414 can be raised from the surface of the plate and moved out of the field of view of the camera (FIG. 4F).

Figure 4G:

In certain embodiments, as shown in FIG. 4O, the wire loop 414 can transfer the selected *C. elegans* 412 to at least one destination plate on the tray. For example, the wire loop 414 with the attached *C. elegans* 412 can then be lowered back into the field of view of the camera 110 to contact a surface of the destination plate (FIG. 4G). The selected *C. elegans* 412 can be moved to the surface of the destination plate from the wire loop 414. This process can be repeated for one or more *C. elegans* (FIG. 4H). In non-limiting embodiments, the wire loop 414 can be coated with bacteria to attach at least one *C. elegans*.

In some embodiments, a capacitive touch sensor can be disposed within the motorized picking assembly and adapted to detect contact between the motorized picking tool and a substrate on the at least one source plate. When the motorized picking tool is lowered to a substrate on the at least one source plate, it can touch the surface of the substrate. Because the surface of the substrate is electrically conductive, touching the motorized picking tool to the surface of the substrate can be detected by the capacitive touch sensor. In some embodiments, the capacitive touch sensor can detect proximity between the motorized picking tool and the substrate on the at least one source plate. The capacitive touch sensor can ensure that the motorized picking tool does not damage the surface of the substrate, as such damage can make it difficult to image the small animals clearly and can allow the small animals to crawl beneath the surface of the surface such that the small animals become inaccessible to the motorized picking tool.

Figure 5A:
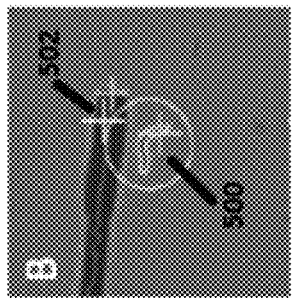
FIGS. 5A-5F are diagrams depicting removal and transfer of one or more selected small organisms in accordance with some embodiments of the disclosed subject matter.
Figure 5B:
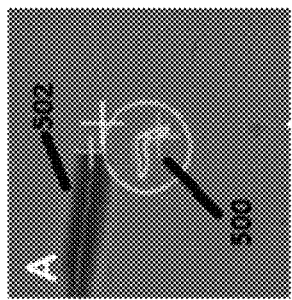

FIGS. 5A-5F are diagrams depicting removal and transfer of one or more selected small animals in accordance with some embodiments of the disclosed subject matter. First, as shown in FIG. 5A, a first small animal 500 can be selected. A motorized picking tool 502 can be centered over the selected first small animal 500. As shown in FIG. 5B, the motorized picking tool 502 can be lowered on to the surface of the substrate containing the selected first small animal. For example, the motorized picking tool 502 can be lowered until surface contact is detected by a capacitive touch sensor.

Figure 5C:
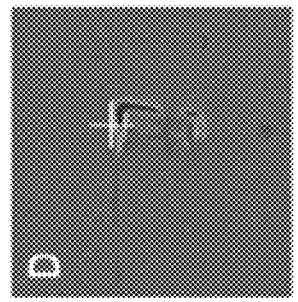
Figure 5D:
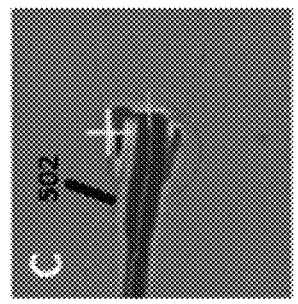
Figure 5E:
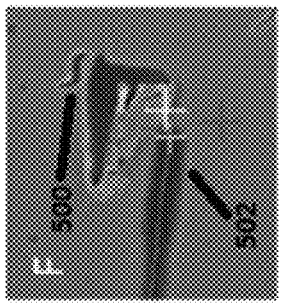
Figure 5F:
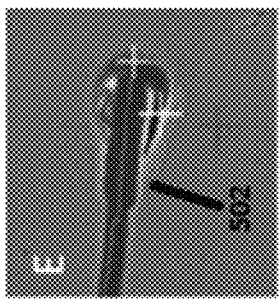

As shown in FIG. 5C, the motorized picking tool 502 can then be swept such that the motorized picking tool 502 removes the selected first small animal 500. As shown in FIG. 5D, the motorized picking tool 502 can be raised from the surface of the substrate and moved out of the field of view of the camera 110. As shown in FIG. 5E, the motorized picking tool 502 can transfer the selected first small animal 500 to the at least one destination plate on the tray. The motorized picking tool 502 can then be lowered back in to the field of view of the camera 110 and in to contact with a surface of the at least one destination plate. As shown in FIG. 5F, the first selected small animal 500 can then be moved to the surface of the at least one destination plate on the tray. For example, the selected first small animal 500 can crawl off the motorized picking tool 502 and on to the surface of the at least one destination plate. This process can be repeated for one or more selected small animals.

The selected first small animal 500 can be swept on to the surface of the at least one destination plate by moving the motorized picking tool 502 across the surface of the at least one destination plate. In some embodiments, the motorized picking tool 502 can be coated in bacteria to adhere the selected first small animal 500 to the motorized picking tool 502. For example, the motorized picking tool 502 can be lowered in to a plate containing bacteria before it is lowered on to the surface of the substrate containing the selected first small animal.

Figure 6B:
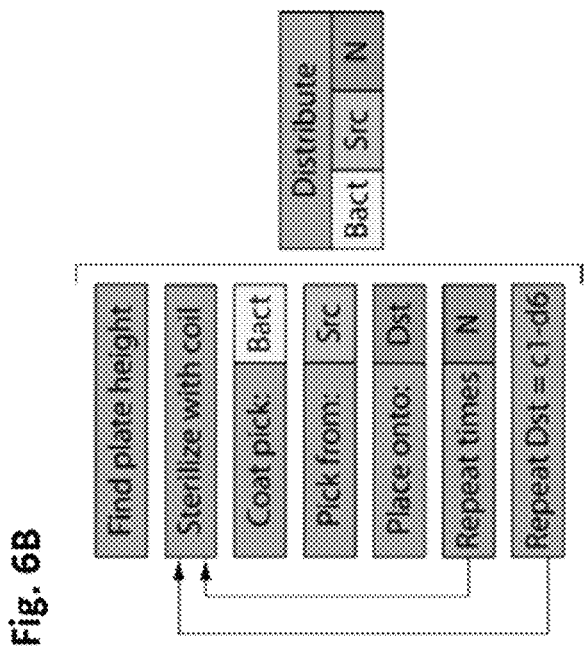
FIGS. 6A-6D are diagrams depicting programming abstractions for the removal and transfer of small organisms in accordance with some embodiments of the disclosed subject matter.
Figure 6D:
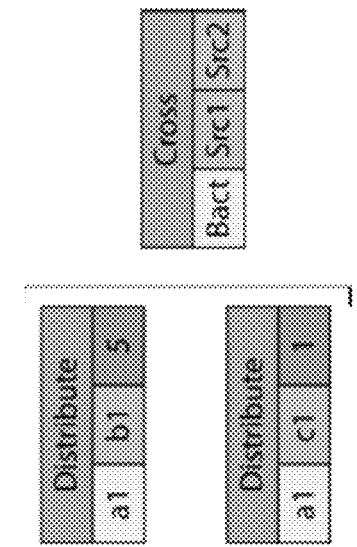
Figure 6A:
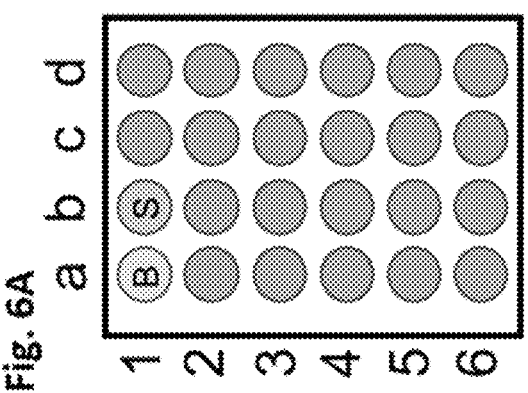
Figure 6C:
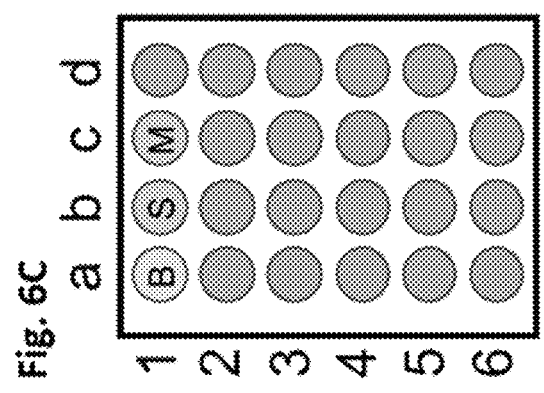

FIGS. 6A-6D are diagrams depicting programming abstractions for the removal and transfer of small animals in accordance with some embodiments of the disclosed subject matter. FIG. 6B depicts an exemplary process that can include sterilizing and coating the motorized picking tool, selecting one or more selected small animals, removing the one or more selected small animals from at least one source plate, and effecting transfer thereof to at least one destination plate. This process can be repeated N times if the removal and transfer of multiple small animals is desired. For example, as depicted in FIG. 6A, plate "B" can contain bacteria for coating the motorized picking tool and plate "S" can contain a plurality of small animals. The small animals in plate "S" can be removed and transferred to the remaining plates as set forth by FIG. 6B. FIG. 6C depicts an exemplary organization where plate "S" contained one type of small animal and plate "M" contains a different type of small animal. FIG. 6D depicts a high-level abstraction to cross the two types of small animal, where 5 small animals from plate "M" are transferred to each remaining plate and 1 small animal from plate "S" is transferred to each remaining plate.

Figure 7A:
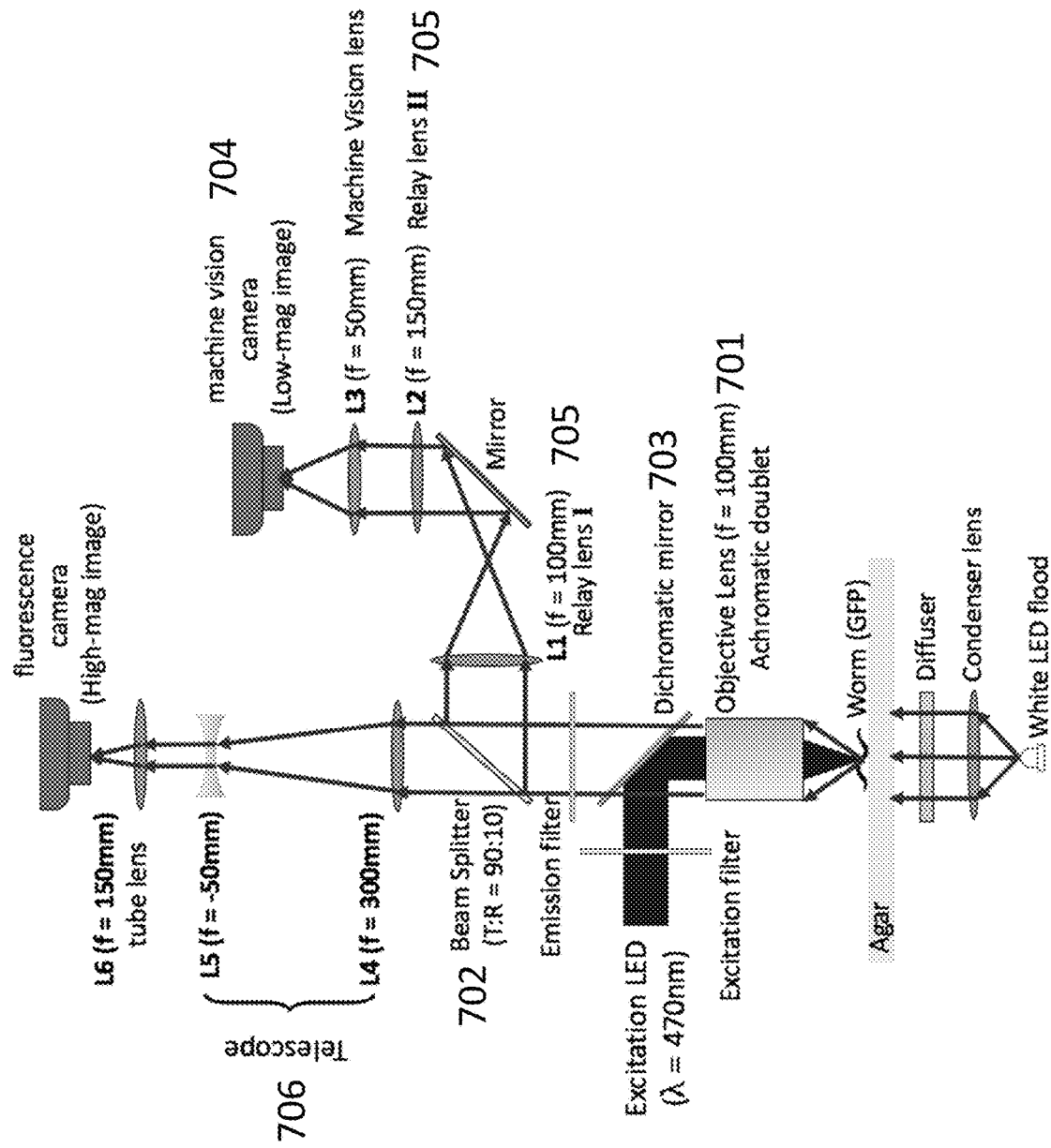
FIG. 7A is a diagram depicting an exemplary system combining fluorescence and bright field microscopy in accordance with some embodiments of the disclosed subject matter.

In certain embodiments, the disclosed subject matter provides a system, which can include a fluorescence microscopy and/or a bright-field microscopy for automated imaging and manipulation of small animals. FIG. 7A is a schematic diagram illustrating an exemplary system which includes both fluorescence and bright-filed microscopy. For example, in order to assay fluorescence of the small animals, the disclosed system can include an epi-fluorescence microscopy. As shown in FIG. 7A, a fluorescence optical system can be arranged in parallel to the optics for bright field imaging.

In non-limiting embodiments, in order to reduce the size of the optical system, the disclosed system can image bright-field images and fluorescence images partially through the same optics. For example, as shown in FIG. 7A, a single objective lens 701 can collect bright field transmitted light and fluorescence emission. A set of fluorescence filters can prepare the excitation and emission wavelengths according to the fluorophore under investigation. A beam splitter 702 or dichroic mirror 703 can reflect some of the light toward a machine vision camera 704 where a low-resolution image can be detected after passing through a relay lens 705 system and a tube lens. The rest of the light can pass through the beam splitter 702 and enter an afocal telescope 706 composed of negative and positive lens, designed to increase the image size. The light can reach a tube lens and a camera where it forms an image. An example of a fluorescent image of GFP-expressing neurons in *C. elegans* acquired through the high magnification pathway is shown in FIG. 7B. GFP-expressing neurons in the head (to the right) and tail (to the left) appear as regions of brighter fluorescence. Approximate field of view 1 mm×1.2 mm.

Figure 7C:
FIG. 7C is an exemplary bright field image of several C. elegans in accordance with some embodiments of the disclosed subject matter.
Figure 7B:
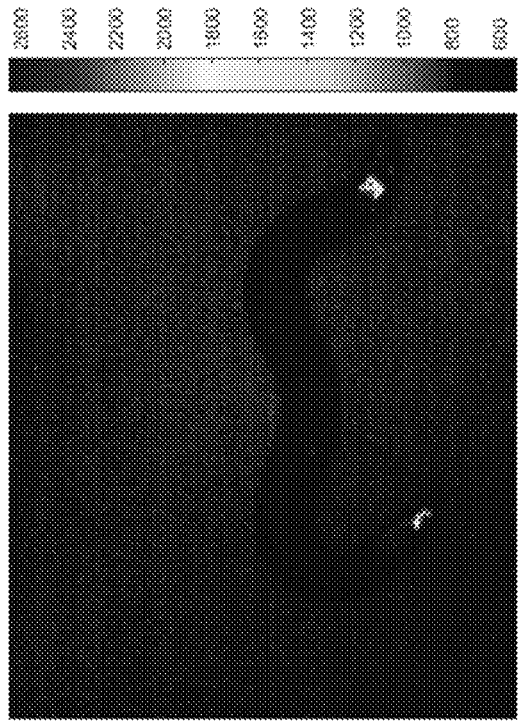
FIG. 7B is an exemplary fluorescence image of a C. elegans in accordance with some embodiments of the disclosed subject matter.

A bright-field image acquired by the low magnification system is shown in FIG. 7C. Worms appear as dark on a light background.

The system for automated imaging and manipulation of a plurality of small animals can be used to increase throughput in labor intensive experiments, increasing the quality of the results. A *C. elegans* procedure that can benefit from such automation is the integration of a transgene into the chromosome to generate a stable line of transgenic animals. For example, to integrate a gene, 20-50 worms carrying an extrachromosomal array that contains many copies of the gene are exposed to ultraviolet light or gamma radiation. During the breakdown and subsequent repair of the animal's DNA, there can be a small probability that the extrachromosomal material is incorporated into the chromosome. Animals with such integrations can be subcultured to generate a stable line of transgenic animals. To identify these lines, the extrachromosomal can be designed such that the worms have a clearly observable behavioral or morphological trait or fluorescent marker.

Worms can be allowed to reproduce for two generations and then 300-1000 individuals that exhibit the desired trait are picked to individual plates and allowed to reproduce for one more generation. As integrant lines can be those in which all progeny carry the desired trait, manual re-screening of all plates after 1-2 weeks can be required. The probability of successfully isolating an integrant line increases with the number of individuals picked at the final step. In certain embodiments, an integrant can be found after picking 800-1000 individuals.

A factor limiting the number of worms picked is the person-hours available to pick worms. Thus, an automated picking strategy not only reduces the manual labor required, but also increases the chance of success. To integrate a transgene using the disclosed apparatus, a user can prepare 5-10 plates containing about 100 F2 (second generation) animals ready to by singled and load them as the source plate on the tray. The "distribute" script, as shown in FIG. 6A-6B can then transfer a single worm onto each of the destination plates. As each tray of destination plates fills, the user removes the tray and loads another containing fresh plates and either the same or a different source plate. After hundreds or thousands of worms are singled, the trays of plates can be stored together for 1-2 weeks to allow reproduction. Finally, to inspect the plates and determine whether any contain integrant lines, the trays can be re-loaded onto the robot, which can inspect each one to determine whether all individuals on each plate display the mutant phenotype.

Figure 8:
FIG. 8 is a diagram depicting an exemplary handheld self-sterilizing loop device in accordance with some embodiments of the disclosed subject matter.

In certain embodiments, the disclosed subject matter provides a handheld self-sterilizing loop device. As shown in FIG. 8, the self-sterilizing loop can be a handheld tool that can be used for manipulating the small animals (e.g., *C. elegans, drosophila* larvae, bacteria, yeast, or other microorganisms). The self-sterilizing loop can include a tip assembly and a handle. In non-limiting embodiments, the tip assembly and the handle can be connected through a threaded connector.

Figure 9:
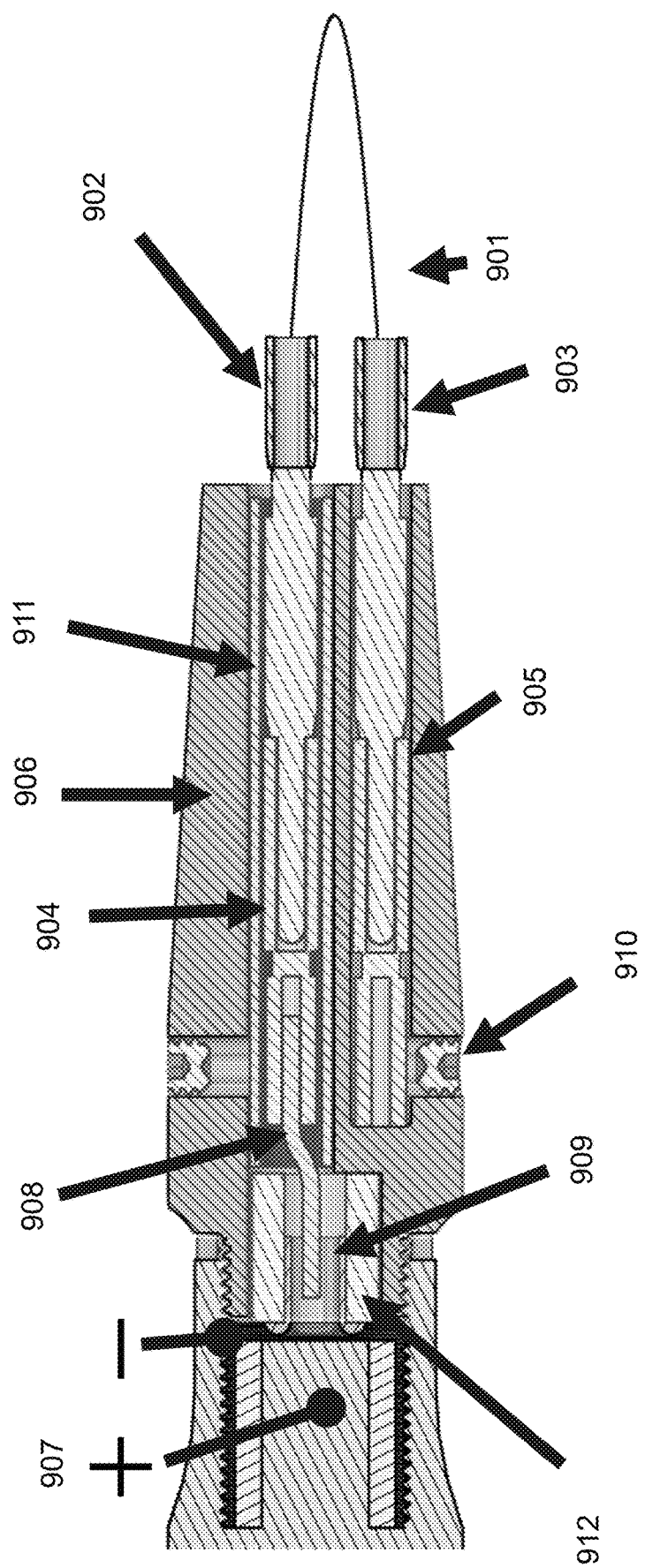
FIG. 9 is a diagram depicting exemplary interior components of the handheld self-sterilizing loop device nose cone interior in accordance with some embodiments of the disclosed subject matter.

In certain embodiments, as shown in FIG. 9, the tip assembly of the self-sterilizing loop can include a wire loop 901, contact pins 902 and 903, contact sockets 904 and 905, and a nose cone 906. The wire loop 901 can be connected to the contact pins 902 and 903 (by crimping, soldering, or other means) that are disposed at the end of the nose cone 906. In non-limiting embodiments, the wire loop 901 can be made of nichrome (nickel-chromium), platinum, platinum-iridium alloy, platinum-rhenium alloy, heat-resistant stainless steel, tungsten, iron-chromium-aluminum or other heat-resistant metals or alloys. The wire is configured to be formed into a loop. In some embodiments, the wire and the two pins 902 and 903 that it is connected to can be removed from sockets 904 and 905 and replaced upon normal wear. The pins can be composed of copper, tin, brass, or other another conductive material. In some embodiments, the tip assembly includes at least two contact pins. The first contact pin 902 can be connected to a plus (+) socket 904, and the second pin 903 can be connected to a negative (−) socket 905. Each pin can be located in a socket. In non-limiting embodiments, the (+) socket 904 can be connected to a plus (+) contact 907 of the battery in the handle via a wire 908 and contact 909. The (−) socket 905 can be directly contacted to the nose cone 906. The nose cone can be an aluminum nose cone. In some embodiments, the nose cone can include an insulating layer 911 for the (+) pin 902 and (+ socket 904). The (+) battery contact 909 can also be mounted within an insulating layer 912. The nose can further include a set screw 910 for fixing the location of the pins and sockets at a predetermined location. For example, a set screw with 3/32" cup point (short side) 1/8" or 3/16" flat (long side) can be inserted into a hole located on the surface of the nose cone 906 to fix the location of the pins in sockets.

In certain embodiments, the nose cone 801 can be configured to be connected to the disclosed system. For example, the motorized picking tool 302 of the disclosed system can be configured to include the nose cone and perform self-sterilization.

In certain embodiments, the self-sterilizing loop device can be a handheld tool that can be used for manipulating the small organisms. The nose cone 801 can be configured to be connected to the handle 802. For example, as shown in FIG. 10, the nose cone can include threads 1001 (e.g., M7×0.5 mm) that can fit into the handle. The (+) battery contact 1002 and the plastic insulator 1003 for the (+) battery contact can be located in the threaded portion 1001 of the nose cone 801 (FIG. 10). In non-limiting embodiments, the self-sterilizing loop can be included as a handheld tool for manual manipulation of the small organisms.

Figure 11:
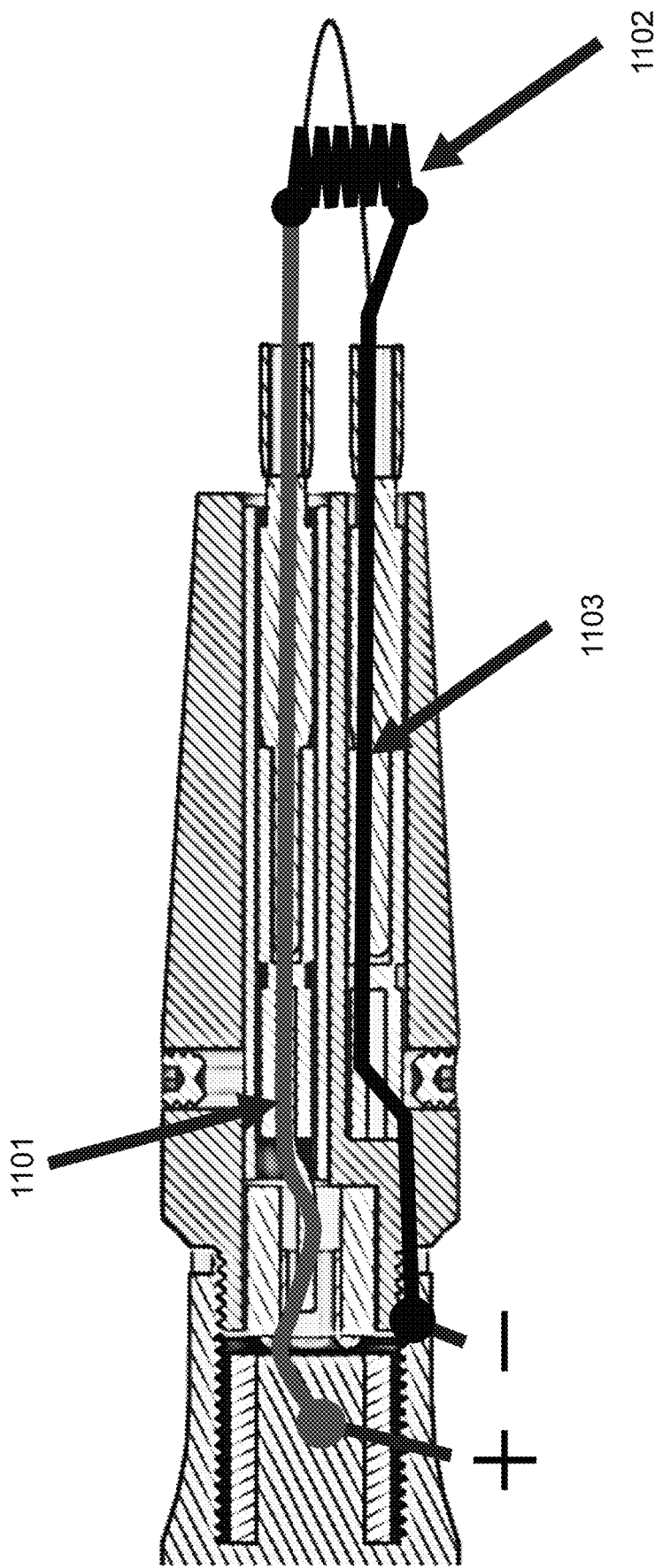
FIG. 11 is a diagram depicting an exemplary current pathway of the handheld self-sterilizing loop device in accordance with some embodiments of the disclosed subject matter.

In certain embodiments, the loop can be configured to be self-sterilized. As shown in FIG. 11, a current 1101 can be generated from the battery and pass through the loop wire 1102 via the pins and sockets heating the wire in excess of 200 degrees C. for the desired time (e.g., 2-3 seconds). The wire loop can be configured to act as a resistor 1102 for generating the predetermined degree of heat. The pathways for positive current can be insulated from the nose cone (e.g., aluminum nose cone). In non-limiting embodiments, the nose cone (e.g., aluminum nose cone) can directly touch the negative (−) battery terminal to complete the (−) portion of the circuit 1103.

Figure 12:
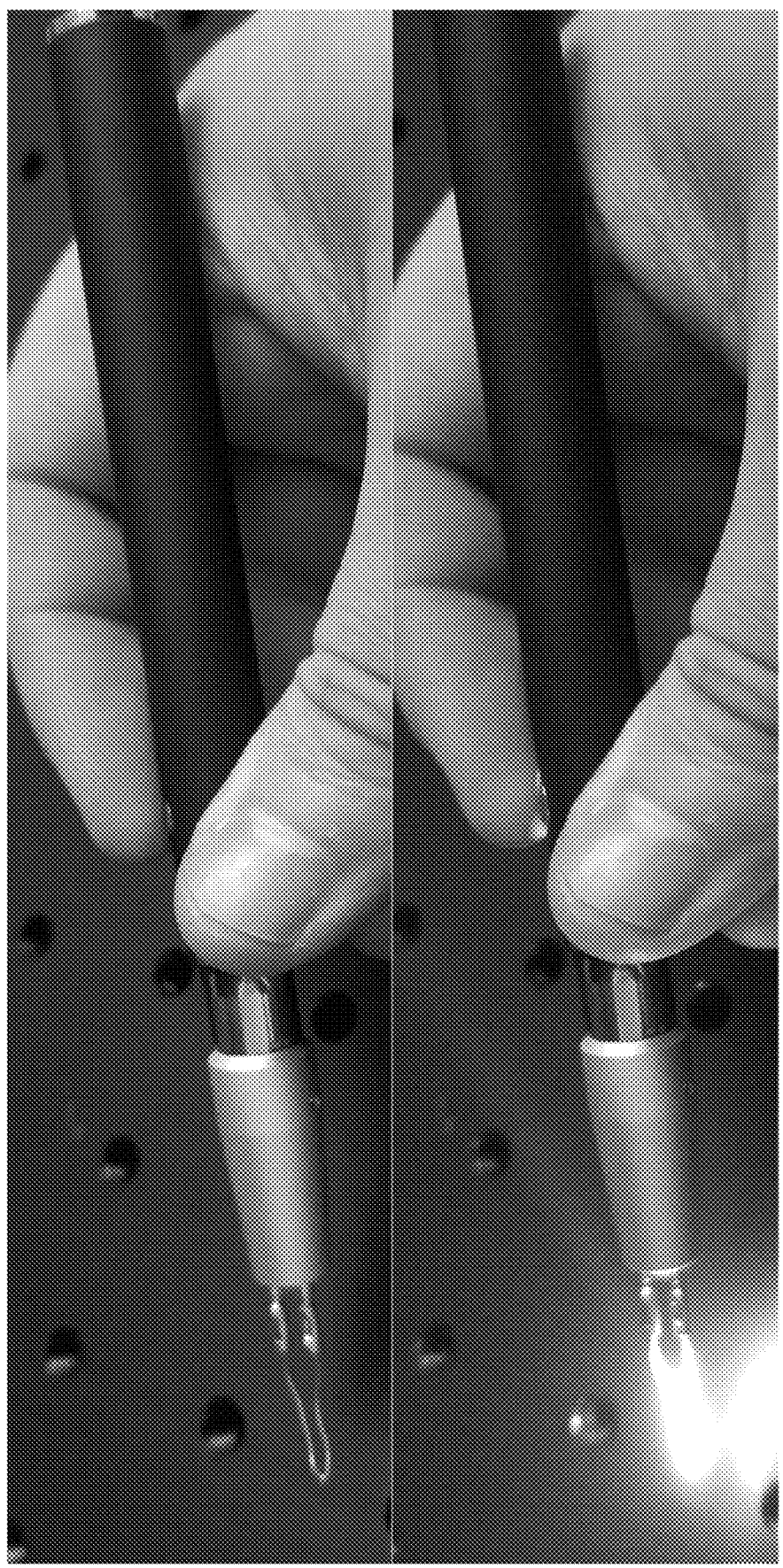
FIG. 12 is a photographic image showing the self-sterilization function of the self-sterilizing loop device in accordance with some embodiments of the disclosed subject matter. When the button is pressed, a current passes through the loop, heating it until it glows red.

In certain embodiments, the self-sterilizing loop can be powered by pressing a button on the surface of the handle (FIG. 12). For example, the current can be generated and heat the wire while the button is activated by pressing. This can allow sterilization to be performed at the touch of a button, without unnecessary movements or need for a separate heat source such as an open flame. In non-limiting embodiments, the self-sterilizing loop device can be connected to a power supply and controlled by a foot pedal controller. A second design is powered by a rechargeable battery within the handle and actuated by a button switch on the handle.

Exemplary processors, such as the processors described herein, can perform the techniques described herein, for example and not limitation, by executing software embodied in one or more tangible, computer-readable media, such as a memory unit. The memory unit can read the software from one or more other computer-readable media, such as a mass storage device or from one or more other sources via a communication interface. The software can cause the processor to execute the particular analysis or response process or particular processes including defining data structures stored in the memory unit and modifying such data structures according to the processes defined by the software.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A handheld tool for manual manipulation of small animals, comprising a handle and a tip assembly, wherein the tip assembly comprises contact pins, contact sockets, and a wire loop, and wherein the contact pins connect to the contact sockets within the tip assembly.

2. The handheld tool of claim 1, wherein the handle comprises a battery.

3. The handheld tool of claim 2, wherein the wire loop is configured to be connected to the battery through the contact pins, and the battery is configured to generate an electrical current that passes through the wire loop and the contact pins, heating the wire loop for sterilization.

4. A method for automated imaging and manipulation of small animals, comprising: identifying at least one parameter for a plurality of small animals; selecting one or more small animals based on the at least one parameter; removing the one or more selected small animals from at least one source plate using a handheld self-sterilizing loop tool comprising a handle, a tip assembly, a wire loop, contact pins, and contact sockets, and wherein the contact pins connect to the contact sockets within the handheld self-sterilizing loon tool.

5. The method of claim 4, wherein the at least one parameter is an approximate size and shape for at least a portion of the plurality of small animals.

6. The method of claim 4, wherein the at least one parameter is a fluorescence signal for at least a portion of the plurality of small animals.

7. The method of claim 4, further comprising taking a lid off the at least one source plate before removing the one or more selected small animals from the at least one source plate.

8. The method of claim 7, further comprising replacing the lid on the at least one source plate after removing the one or more selected small animals from the at least one source plate.

9. The method of claim 5, wherein the approximate size and shape for the at least a portion of the plurality of small animals is identified with a camera.

10. The method of claim 9, further comprising aligning an illuminator with a position of the camera such that the illuminator illuminates upwards into the camera.

11. The method of claim 4, further comprising sterilizing the wire loop by generating a current that passes through the wire loop and contact pins within the handheld self-sterilizing loop tool.

12. The method of claim 4, wherein a battery in the handle is configured to generate a current heating the wire loop to a temperature in excess of 1000 degrees Fahrenheit.

* * * * *